United States Patent [19]

Weinstein et al.

[11] 4,049,498
[45] Sept. 20, 1977

[54] METHODS FOR THE PREPARATION OF SEMI-SYNTHETIC AMINOCYCLITOL AMINOGLYCOSIDE ANTIBIOTICS

[75] Inventors: Marvin Joseph Weinstein, East Brunswick; Peter John Lovell Daniels, Cedar Grove; Gerald Howard Wagman, East Brunswick; Raymond Thomas Testa, Verona, all of N.J.

[73] Assignee: Schering Corporation, Kenilworth, N.J.

[21] Appl. No.: 750,944

[22] Filed: Dec. 15, 1976

Related U.S. Application Data

[60] Division of Ser. No. 476,638, June 5, 1974, Pat. No. 4,011,390, which is a continuation-in-part of Ser. No. 443,052, Feb. 15, 1974, abandoned.

[51] Int. Cl.$^2$ ............................................. C12D 9/20
[52] U.S. Cl. ..................................................... 195/96

[58] Field of Search ............................................ 195/96

[56] References Cited

U.S. PATENT DOCUMENTS

| 3,669,838 | 6/1972 | Shier et al. | 260/210 AB |
| 3,832,286 | 8/1974 | Weinstein et al. | 260/210 AB |
| 3,907,771 | 9/1975 | Weinstein et al. | 260/210 AB |

*Primary Examiner*—Lionel M. Shapiro
*Attorney, Agent, or Firm*—Carver C. Joyner; Stephen B. Coan; Raymond A. McDonald

[57] ABSTRACT

*Micromonospora inyoensis* strain 155OF-1G NRRL 5742 is incapable of producing antibiotics unless an aminocyclitol is added to the fermentation medium. When such a compound is added, antibiotics are produced, said antibiotics being analogs of known aminoglycoside antibiotics differing therefrom with respect to the aminocyclitol subunit.

9 Claims, No Drawings

METHODS FOR THE PREPARATION OF SEMI-SYNTHETIC AMINOCYCLITOL AMINOGLYCOSIDE ANTIBIOTICS

The subject matter of this application was divided out of co-pending application Ser. No. 476,638, filed June 5, 1974, now U.S. Pat. No. 4,011,390, which application is a continuation-in-part of application serial number 443,052, filed Feb. 15, 1974 (now abandoned).

This invention relates to novel antibiotics, to acid addition salts thereof and to the preparation of the antibiotics by a novel microbiological process. More particularly, this invention relates to a class of antibiotics which are designated Antibiotics Mu-1, Mu-2, Mu-4, Mu-5 and Mu-6. These antibiotics were formerly referred to collectively as "mutamicins" and individually as mutamicin 1, mutamicin 2, mutamicin 4, mutamicin 5 and mutamicin 6, respectively.

The respective antibiotics are elaborated by a mutant strain of *Micromonospora inyoensis* herein designated *Micromonospora inyoensis* strain 1550F-1G, This mutant strain is incapable of producing an antibiotic when cultivated under submerged aerobic conditions in an aqueous nutrient medium absent an aminocyclitol, or an acid addition salt thereof. However, when certain of such compounds are added to the fermentation medium, antibiotics are produced. When 2-deoxystreptamine is added to the fermentation, sisomicin is produced.

PRIOR ART

In U.S. Pat. No. 3,669,838, issued June 13, 1972, Shier, W. T. et al. describe and claim a process whereby mutant strains of known microorganisms produce antibiotics by the addition of aminocyclitols to the fermentation medium. The aminocyclitols added become a subunit of the elaborated antibiotic. Methods for producing mutants are generally known in the art include such techniques as exposure of the "parent" microorganism to mutantagenic agents such as nitrogen mustards, ultraviolet light, gamma radiation or the like. Following the exposure, survivors are selected and new colonies started therefrom. Those having the capacity to perform the process of this invention may be determined by the procedure described in column 2, lines 13–32 of the aforementioned patent.

DESCRIPTION OF THE INVENTION

This invention may be described as a process for producing novel antibiotics which comprises fermenting *Micromonospora inyoensis* strain 1550F-1G in an aqueous nutrient medium, adding to the fermentation a compound of the formula:

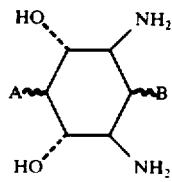

wherein A is a member selected from the group consisting of hydrogen, amino, hydroxy and ($C_1$-$C_8$) alkoxy, B is a member selected from the group consisting of hydrogen and hydroxy, wherein the wavy lines connecting A and B to the ring nucleus denote that such groups may be in any of the possible stereoisomeric forms with the proviso that when B is hydrogen and A is hydroxy, A must be cis to the hydroxy groups adjacent thereto and with the further proviso that when A is amino, it must be trans to the hydroxy groups adjacent thereto; continuing the fermentation until a composition of matter having substantial antibacterial activity is produced and isolating a novel antibiotic therefrom.

In its composition of matter aspect, this invention may be described as being directed to the aminocyclitolaminoglycoside antibiotics which are analogs of known compounds of this class differing therefrom with respect to the structure of the aminocyclitol subunit.

This invention is also directed to the use of said novel aminoglycoside antibiotics in the control or destruction of bacterial species, especially species which have developed resistance to aminoglycoside antibiotics currently being used.

Sisomicin is an elaborate of unmutated *Micromonospora inyoensis* and has the chemical name and structure below.

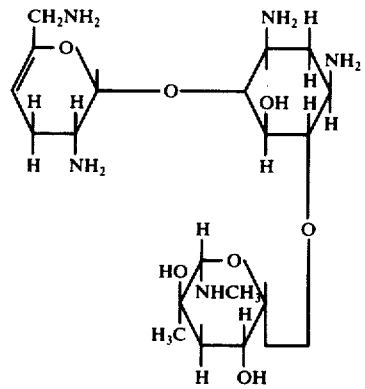

O-2,6-Diamino-2,3,4,6-tetradeoxy-α-D-glycero-hex-4-eno-pyranosyl-(1→4)-O-[3-deoxy-4-C-methyl-3-(methylamino)-B-L-arabinopryanosyl-(1→6)]-2-deoxy-D-streptamine.

The moiety in the upper right of Formula I is derived from 2-deoxystreptamine and is the one moiety by which the Antibiotics Mu-1, Mu-2, Mu-4, Mu-5 and Mu-6 differ from each other and from known aminoglycoside antibiotics.

Aminocyclitols are well known in the field of antibiotic chemistry and are usually saturated carboxycyclic ring compounds having amino groups and hydroxyl groups attached to the ring. They may also be described as cyclic polyols wherein one or more hydroxyl groups have been replaced by an amino group.

THE MICROORGANISM

The parent microorganism (*Micromonospora inyoensis*) is described in the Journal of Antibiotics (Japan) Vol. XXIII, No. 11, pages 551–558 (1970) in a publication by M. J. Weinstein, et al.

*Micromonospora inyoensis* strain 1500F-1G exhibits growth characteristics that are similar to *Micromonospora inyoensis* (the microorganism from which it is derived). *M. inyoensis,* the unmutated microorganism, is deposited with U.S. Department of Agriculture, Northern Utilization Research and Development Division, Peoria, Illinois, where it was assigned the numerical designation NRRL 3292. A culture of *M. inyoensis* strain 1550-1G has been deposited with the above-mentioned depository where it was assigned the numerical designation NRRL 5742.

The following tables set forth a number of taxonomical, biochemical morphological properties of the microorganism. In the description of the microorganism, two color designates are used. The first is a color name taken from the "Descriptive Color Name Dictionary" by Taylor, Knoche and Granville published by the Container Corporation of America (1950) U.S.A., with a color chip number corresponding to the color name, the chip number being taken from "The Color Harmony Manual," 4th Edition, 1958 published by the Container Corporation of America. The second designate consists of a color name and number which refers to the synonym or near synonym found in the National Bureau of Standards, Circular 553, November 1, 1955, (U.S.A.)

TABLE I

Morphology of Micromonospora inyoensis Strain 1550F-1G NRRL 5742
Medium: 3% NZ Amine Type A, 1% Dextrose, 1.5% Agar
Observations

| Macroscopic | Microscopic |
|---|---|
| Growth poor, not sufficient for characterization | |

TABLE II

Colony Description of Micromonospora inyoensis Strain 1550F-1G NRRL 5742 on Various Media or Conditions

| Medium or Condition | Observations |
|---|---|
| Sucrose | Utilized |
| Temperature | Grows well at 28° and 37° C |
| | No growth at 50° C |
| Aerobic or Anaerobic | Aerobic |
| Czapeks Medium (Glucose) | Growth fair to poor, plicate - membranous, no diffusible pigment g3ic light amber - dark orange yellow 72 |
| Asparagine Glucose Medium | Growth fair to poor, flat to membranous, no diffusible pigment g3ic light amber - dark orange yellow 72 |
| Calcium Malate Agar | Growth poor, flat, no diffusible pigment g3ic light amber - dark orange yellow 72 |
| Nitrate Reduction | Variable |
| Ordinary Agar (Water Agar) | Growth poor, insufficient for description |
| Nutrient Agar | Growth fair to poor, flat to slightly wrinkled g4ne luggage tan - strong brown 55 to g4pn chocolate brown - dark brown 59 |
| Loffler's Serum Medium (Difco) | Growth fair, substrate partially liquified g5pe terracotta - strong brown 55 |
| Potato Plug | No growth |
| Peptone Glucose Agar | Growth fair to poor, flat to slightly furrowed, no diffusible pigment produced g4ne luggage tan - strong brown 55 |
| Egg Agar (Dorset Egg Medium - Difco) | Growth poor, insufficient for characterization |
| Gelatin Medium | Growth fair to poor, flat to slightly ridged, no diffusible pigment produced, gelatin weakly hydrolyzed g4le turf tan - light brown 57 |
| Starch Agar | Growth fair, flat, no diffusible pigment, starch weakly hydrolyzed only directly under colony g3le yellow maple - strong yellowish brown 74 to black |
| Tyrosine Medium | Growth fair to poor, flat, slight darking of medium g4le turf tan - light brown 57 |
| Litmus Milk (Difco) | Peptonized, acid reaction |
| Cellulose Medium | Cellulose poorly decomposed (hydrolysis of cellulose weak) |
| Bennett's Agar | Growth good, membranous - |

TABLE II-continued

Colony Description of Micromonospora inyoensis Strain 1550F-1G NRRL 5742 on Various Media or Conditions

| Medium or Condition | Observations |
|---|---|
| | plicate, no diffusible pigment black |
| Emerson's Agar | Growth good, membranous, no diffusible pigment g3ni clove brown, dark yellowish brown 78 |
| Tomato Paste Oatmeal Agar | Growth fair, raised, ridged, no diffusible pigment g4nc russet orange, strong orange 50 |
| Glucose Yeast Extract Agar | Growth good, membranous, no diffusible pigment black |
| Potato Slice | + CaCO$_3$ + + + growth, black − CaCO$_3$ no growth |
| Tyrosine Agar Yeast Extract | Growth good, membranous, crystals dissolved, light brown diffusible pigment produced |
| Tyrosine - Beef Extract Observations at 2, 7 and 14 days (after Gordon and Smith, J. Bact. 69:147)(1955) | Growth fair to poor, crystals weakly dissolved, brownish diffusible pigment produced only on cross-hatched method |
| Peptone Iron Agar Observations at 2, 7 and 14 days | No growth, no reaction |

TABLE III

Utilization of Nitrogen Sources by Micromonospora Inyoensis Strain 1550F-1G NRRL 5742

| Nitrogen Source | Observations |
|---|---|
| +1% Glucose 0.5% Difco Yeast Extract | Growth good, membranous, no diffusible pigment produced black |
| 1.0% NZ Amine Type A | Growth good, membranous, plicate g4nc russet orange, strong orange 50 to black |
| 1% Asparagine | Growth poor, insufficient for description |
| 1% Glutamic Acid | Growth poor, insufficient for description |
| 1% Sodium Nitrate | Growth poor, insufficient for description |
| 1% Ammonium Nitrate | Growth poor, insufficient for description |

TABLE IV

Utilization of Carbohydrates by Micromonospora Inyoensis Strain 1550F-1G NRRL 5742

| | Growth |
|---|---|
| Control | ± poor |
| D-Arabinose | ± poor |
| L-Arabinose | ± poor |
| Dulcitol | ± poor |
| D-Galactose | + fair |
| D-Glucose | + + good |
| Glycerol | ± poor |
| I-Inositol | ± poor |
| D-Lactose | ± poor |
| D-Levulose | + fair |
| D-Mannitol | ± poor |
| Mannose | + + + good |
| Melibiose | ± poor |
| Melizitose | ± poor |
| Raffinose | ± poor |
| L-Rhamnose | ± poor |
| D-Ribose | + fair |
| Salicin | ± poor |
| Sucrose | + fair |
| D-Xylose | + + good |

The Fermentation

In order to produce the Antibiotics Mu-1, Mu-2, Mu-4, Mu-5 and Mu-6, a lyophilized culture or cells from a slant culture, of *Micromonospora inyoensis* strain 1550-1G NRRL 5742 is transferred to a sterile inoculum medium. The medium is an aqueous one containing assimilable sources of nitrogen, carbohydrates and the usual compliment of trace metals. The inoculated medium is permitted to incubate under aerobic conditions at from about 24° to about 40° C, preferably about 35° C for from about 2 to about 5, preferably about 3 days. The pH is maintained in the range of from about 6.0 to about 8.0, preferably from about 6.8 to about 7.4.

The so-produced inoculum is aseptically transferred to a fermentation medium, which medium may be the same as or different from the inoculum medium. An aminocyclitol may be added to the fermentation medium before sterilization, at the time of inoculation or up to 48 hours after inoculation. Further, the aminocyclitol which may be in the form of an acid addition salt is usually dissolved in water, sterile filtered and added to the fermentation medium. In general, the concentration of the compound is from about 100 to about 1500 mcg/ml. of fermentation broth. The fermentation is conducted under aerobic conditions, and under about the same conditions of temperature and pH as is the inoculum. Peak antibiotic production is determined by the assay used for sisomicin [see J. Antibiotics (Japan) Vol. XXIII]. The antibiotics are isolated from the fermentation and from co-produced minor components having antibacterial activity by methods generally used in the art for aminoglycoside antibiotics. For example, the acidified broth is separated from the mycelium. After neutralization, the antibiotic is adsorbed from the broth by ion exchange techniques and desorbed from the ion exchange resin yielding an aqueous solution rich in antibiotic. The solution may be lyophilized to yield the antibiotics in solid form, or alternatively, the solution may be subjected to purification techniques, such as chromatography to yield the novel antibiotics in substantially pure form free from co-produced minor components.

The Antibiotics

As stated above, the Antibiotics Mu-1, Mu-2, Mu-4, Mu-5 and Mu-6 are analogs of known aminoglycoside antibiotics but differ therefrom and from each other with respect to the structure of the aminocyclitol subunit. The major components isolated from the fermentation of Micromonospora inyoensis strain 1550F-1G NRRL 5742 are analogs of sisomicin differing therefrom only in the structure of the aminocyclitol subunit. Thus, they may be described as tricyclic aminocyclitol-aminoglycoside antibiotics having the general formula:

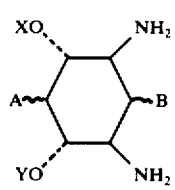

wherein X is 2,6-diamino-2,3,4,6-tetradeoxy-α-D-glycero-hex-4-enopyranose; Y is 3-deoxy-4-C-methyl-3-(methylamino)-β-L-arabinopyranose; A is a member selected from the group consisting of hydrogen, amino, hydroxy and alkoxy ($C_1$-$C_8$); B is a member selected from the group consisting of hydrogen, and hydroxy; and wherein the wavy lines connecting A and B to the ring nucleus denotes that such groups may be in any of the possible stereoisomeric forms with the proviso that when B is hydrogen and A is hydroxyl, A must be cis to the glycosyl groups adjacent thereto and with the further proviso that when A is amino, it must be trans to the glycosyl groups adjacent thereto.

Antibiotic Mu-1 is that analog of sisomicin wherein 2-deoxy-streptamine is replaced by streptamine and may be represented by formula III below.

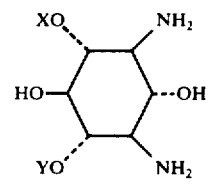

III wherein X and Y are as defined above.

Antibiotic Mu-2 is that analog of sisomicin wherein 2-deoxy-streptamine is replaced by 2,5-dideoxystreptamine and may be represented by formula IV below:

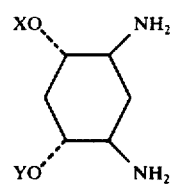

IV wherein X and Y are as defined above.

The precursor for Mu-2 (i.e. 2,5-dideoxystreptamine) is novel and may be prepared by a novel synthesis described in the application of Peter J. L. Daniels and Mohammad Mehdi Nafissi Varchei, entitled, "Process for the Preparation of 2,5-dideoxystreptamine and of a Novel Intermediate Therefor", Serial No. 443,051, filed Feb. 15, 1974.

Antibiotic Mu-4 is that analog of sisomicin wherein 2-deoxystreptamine is replaced by 2-epistreptamine (myo-inoso-1,3-diamine) and may be represented by formula V below:

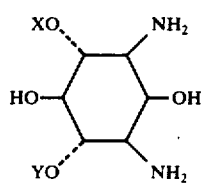

V wherein X and Y are as defined above.

Antibiotic Mu-5 is that analog of sisomicin wherein 2-deoxystreptamine is replaced by 1,3,5-triaminocyclohexane-4,6-diol and may be represented by formula VI below:

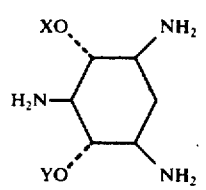

VI wherein X and Y are as defined above.

Antibiotic Mu-6 is that analog of sisomicin wherein 2-deoxystreptamine is replaced by 5-epi-2-deoxystreptamine and may be represented by formula VII below:

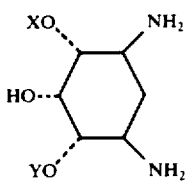

VII wherein X and Y are as defined above.

The antibiotics readily form non-toxic salts with organic and inorganic acids, such as for example, hydrochloric, sulfuric, phosphoric, acetic, stearic, propionic, tartaric, maleic, benzoic, acid and the like. In general, the salts are water soluble and may be obtained by concentration or lyophilization of an aqueous solution thereof or by precipitation with a water miscible organic solvent preferably a lower aliphatic alcohol or ketone.

The antibiotics also form non-toxic Schiff baseoxazolidine derivatives when reacted with aldehydes under standard reaction conditions. Exemplary of the aldehydes whose use is contemplated are acetaldehyde, propionaldehyde, butyraldehyde, crotonaldehyde, fural, cyclopentylacetaldehyde, vanillin, veratraldehyde, benzaldehyde, p-nitrobenzaldehyde, salicylaldehyde, pyridoxal and the like. These condensation products are not appreciably soluble in water but are soluble in most commonly used organic solvents such as chloroform, methanol, acetone, ethyl acetate and the like.

Preparation of Precursors

The compounds which are utilized by *Micromonospora inyoensis* strain 1550F-1G NRRL 5742 to produce the antibiotics are generally obtained from one of two sources. The first is by the hydrolysis of known antibiotics followed by separation, isolation and recovery of the aminocyclitol subunit. Exemplary of the compounds obtained in this manner are streptamine and 2-deoxystreptamine, the last named compound being obtained from the hydrolysis of gentamicin or kanamycin. The preparation of streptamine by the stepwise hydrolysis of streptomycin is described by Fried, J. et al. in the J. Biological Chemistry, 162, 381 (1946).

The second source by which the intermediate compounds are obtained is by chemical synthesis from readily available starting materials. Included in this group is the aminocyclitol of Antibiotic Mu-2 (2,5-dideoxystreptamine) which may be prepared by treatment of the dicarbamate of 2-deoxystreptamine (VIII) with iodomethyltriphenylphosphorane to form the 5-iodo derivative (IX). The iodo group is removed via hydrogenolysis to yield the 2,5-dideoxystreptamine carbamate which compound in the presence of aqueous acid yield 2,5-dideoxystreptamine (X) as an acid addition salt. The free amine is generated in the usual manner (e.g. by treatment with aqueous alkali).

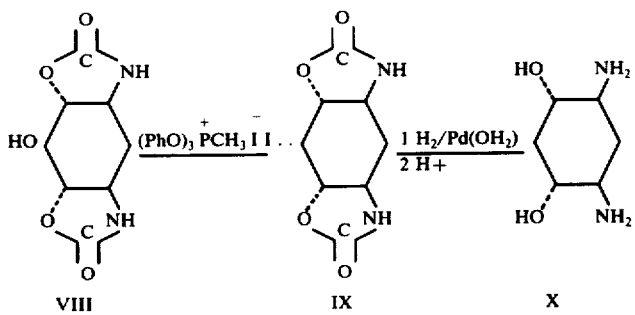

By analogy, treatment of the dicarbamate of 2-deoxystreptamine (VIII) with alkylating agents such as methyl iodide under the usual conditions yields the 5-O-methyl derivative (XI). Hydrolysis of this intermediate under mild conditions affords the 5-alkoxy-analog of 2-deoxystreptamine (XII).

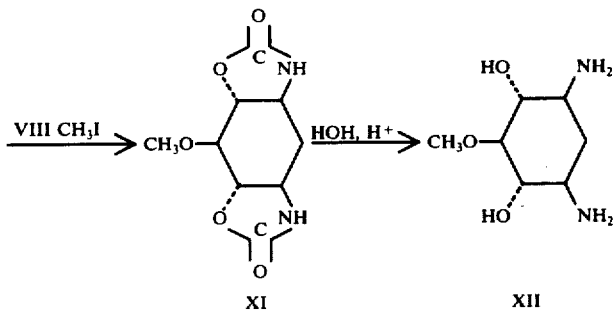

By cleaving an N,N-diacyl derivative of 2-deoxystreptamine (XIII) with periodate, a 1,3-dialdehyde (XIV) is produced. Treatment of the dialdehyde with nitromethane under alkaline conditions effects ring closure and the insertion of a nitro group at the 5-position (XV). Reduction of the nitro group to an amino group followed by hydrolysis of the N,N-diacyl functions to the free amine affords the 5-amino analog (XVI) of 2-deoxystreptamine (1,3,5-triaminocyclohexane-4,6-diol).

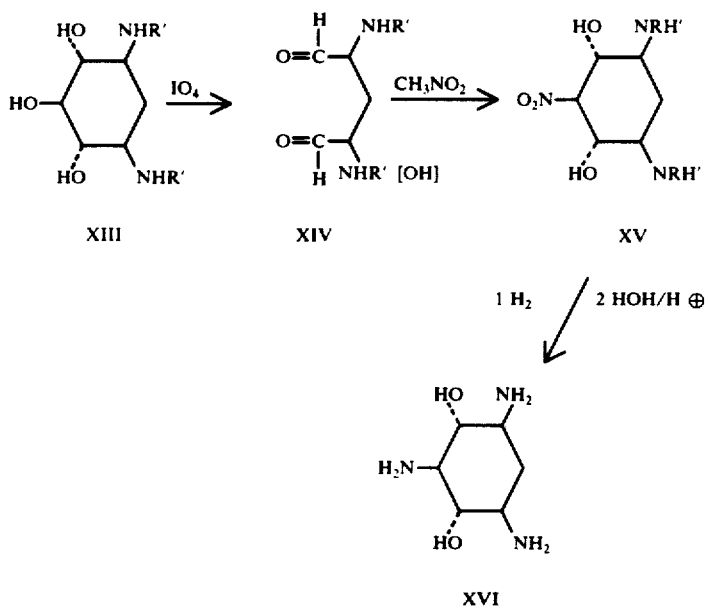

Other aminocyclitol precursors suitable for utilization in this invention may be prepared as described below:

2-Epi-streptamine (see Antibiotic Mu-4) may be prepared by the method described by Tetsue Suami et al. in the Journal of Organic Chemistry 33, No. 7, 2831-2834 (1968).

PREPARATION 1

2-Deoxy-myoinosa-1,3,5-triamine

Treat 13.0g of (1,3/2,4,6)-4,6-diacetamido-2-aminocyclohexane-1,3-diol with 100 ml. of 6N hydrochloric acid at reflux for 18 hours. Cool the reaction mixture to room temperature (20° C) and treat with Amberlite IRA-401S (OH form) until alkaline. Filter and evaporate the alkaline solution to obtain 7.0 g of the title product, m.p. 192°-194° C (dec.).

Anal. Calculated: $C_6H_{15}N_3O_2$; C = 44.70%; H = 9.38% Found: C = 44.84%; H = 9.32%.

2-Deoxy-5-epistreptamine may be prepared from compound XVII which may be prepared by the method of Hasagawa and Sable Tetrahedron, 25, 35, 67 (1969) the ultimate step in the sequence being the following:

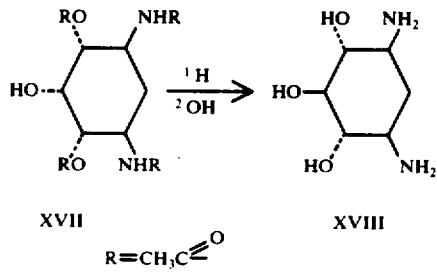

PREPARATION 2

2-Deoxy-5-epistreptamine

Treat 0.8g of compound XVII with 12 ml. of 6N hydrochloric acid at reflux for 3 hours. Cool the solution to room temperature (20° C) and treat with Amberlite IRA-401S (OH form) until alkaline. Filter and evaporate to a residue and chromatograph on silica gel using the lower phase of a chloroform: methanol: conc. ammonium hydroxide (1:1:1) solvent system as eluant. The fractions containing the major component are collected and evaporated to afford the title compound (XVIII) as a white amorphous solid.

Mass spectrum: $m/e = 163$ $(M+1)^+$

NMR: triplet $\delta 4.14$ ppm (J = 2.5 Hz, 1H, H-5 eq). $\delta 3.8 - 2.85$ ppm, 4H, multiplets. $\delta 2.34$ ppm, 1H, doublet of triplets J = 3.5, 12Hz, H-2 eq. $\delta 1.53$ ppm, 1H, quartet, J = 12Hz, H-2ax.

Physiochemical Data

The structures of the Antibiotics were determined by conventional chemical analyses. Data relating to the mass spectra of compounds are set forth below, structural assignments based thereon are in accordance with the publication by Daniels, P.J.L. et al. in *Chemical Communications* No. 24 1629-31 (1971).

Table 5

| Antibiotic Mu-1 | | Mass Spectral Data Antiobiotic Mu-2 | |
|---|---|---|---|
| Peaks at (M/e) | Assignment | Peaks at (M/e) | Assignment |
| 464 | $(M+1)^+$ | 432 | $(M+1)^+$ |
| 446 | $(M - NH_3)^+$ | 431 | $M^+$ |

Table 5-continued

Mass Spectral Data

378  $\begin{bmatrix} CH_2NH_2 \\ | \\ M-C=O \\ | \\ HC=CH_2 \end{bmatrix}$   414  [M − NH$_3$]·
346  $\begin{bmatrix} CH_2NH_2 \\ | \\ M-C=O \\ | \\ C=CH_2 \end{bmatrix}$

| | | | |
|---|---|---|---|
| 366) | | | |
| 348) | disaccharide | 336) | |
| 338) | ion series | 316) | dissacharide |
| 320) | | 306) | ion series |
| | | 288) | |
| 333) | disaccharide | 301) | |
| 315) | ion series | 283) | disaccharide |
| | | 274) | ion series |
| 207) | | 255) | |
| 189) | streptamine | | |
| 179) | ion series | 175) | |
| 161) | | 157) | 2,5-dideoxy- |
| 127) | unsaturated | 147) | streptamine |
| | monosaccharide | 129) | ion series |
| 160) | | 160) | |
| 142) | garosamine | 142) | garosamine |
| 118) | ion series | 118) | ion series |
| | | 127) | unsaturated |
| | | | monosaccharide |

| Antibiotic Mu-4 | | Antiobiotic Mu-5 | | Antiobiotic Mu-6 | |
|---|---|---|---|---|---|
| Peaks at | Assignment | Peaks at | Assignment | Peaks at | Assignment |
| 464 | (M+1)$^+$ | 447 | (M+1)$^+$ | 448 | (M+1)$^+$ |
| 446 | (M − NH$_3$)$^+$ | 446 | M$^+$ | 447 | M$^+$ |
| 378 | $\begin{bmatrix} CH_2NH_2 \\ | \\ M-C=O \\ | \\ C=CH_2 \end{bmatrix}^+$ | 349) | disacchar- | 350) | disacchar- |
| | | 331) | ride ion | 332) | ride ion |
| | | 321) | series | 322) | series |
| | | 303) | | 304) | |
| 366) | | | | | |
| 348) | disaccha- | 316) | disaccha- | 317) | |
| 338) | ride ion | 288) | ride ion | 299) | disaccha- |
| 320) | series | 270) | series | 289) | ride ion |
| | | | | 271) | series |
| 333) | disaccha- | 190) | triamino | | |
| 315) | ride ion | 162) | dihydroxy | 160) | |
| | series | 144) | cyclohex- | 142) | garosamine |
| | | | ane ions | 118) | ion series |
| 207) | | | | | |
| 189) | disaccha- | 160) | | 127) | unsaturated |
| 179) | ride ion | 142) | garosamine | | monosaccha- |
| 161) | series | 118) | ion series | | ride |
| 160) | | 127) | unsaturated | 191) | 5-epi-2- |
| 142) | garosamine | | monosaccha- | 173) | deoxy- |
| 118) | ion series | | ride | 163) | streptamine |
| | | | | 145) | ion series |
| 127) | unsaturated | | | | |
| | monosaccha- | | | | |
| | ride | | | | |

(M/e) = mass to charge ratio

Chromatographic Data

The antibiotics may be distinguished from sisomicin and from each other by chromatographic techniques known in the art. For example, when chromatographed on Whatman No. 1 paper in the lower phase of a solvent system consisting of chloroform, methanol and 17% ammonium hydroxide (2:1:1) for 4 hours the following patern is observed:

Rt (4 hours)

Sisomicin = 0.23
Antibiotic Mu-1 = 0.11
Antibiotic Mu-2 = 0.35
Antibiotic Mu-4 = 0.15
Antibiotic Mu-5 = 0.22
Antibiotic Mu-6 = 0.08

Using sisomicin as reference, the antibiotics have the following R sisomicin values:

Sisomicin = 1.0
Antibiotic Mu-1 = 0.48
Antibiotic Mu-2 = 1.52
Antibiotic Mu-4 = 0.65
Antibiotic Mu-5 = 0.95
Antibiotic Mu-6 = 0.35

EXAMPLE 1

Fermentation of Micromonospora Inyoensis Strain 1550F-1G NRRL 5742 Inoculum Preparation Inoculum — Strain 1

Under aseptic conditions, add a lyophilized culture (or cells obtained from a slant culture) of *M. inyoensis* strain 1550F-1G to a 300 ml. shake flask containing 100 ml. of the following sterile medium:

| | |
|---|---|
| Beef extract | 3 g |
| Tryptose | 5 g |

-continued

| Yeast extract | 5 g |
|---|---|
| Dextrose | 1 g |
| Starch | 24 g |
| Calcium carbonate | 2 g |
| Tap water | 1000 ml. |

Incubate the flask and its contents for 2-5 days at 35° C on a rotary shaker (280 rpm, 2 inch stroke).

Inoculum — Stage 2

Aseptically transfer 25 ml. of the fermentation medium of germination stage 1 to a 2-liter shake flask containing 500 ml. of the aforedescribed sterile germination medium. Incubate the flask and its contents for 3 days at 28° C on a rotary shaker (280 rpm, 2 inch stroke).

Fermentation Stage

Aseptically transfer 500 ml. of the inoculum obtained from germination stage 2 to a 14 liter fermentation tank containing 9.5 liters of the following sterile medium:

| Dextrin | 50 g |
|---|---|
| Dextrose | 5 g |
| Soybean meal | 35 g |
| Calcium carbonate | 7 g |
| Cobalt chloride | $10^{-6}$ molar |
| Tap water | 1000 ml. |
| Antifoam (GE 60) | 10 ml. |

Prior to sterilizing the aforementioned medium, adjust the pH to 8 and add an aqueous solution containing 8.0g of streptamine. Ferment the contents under aerobic conditions for 48-240 hours, with stirring at 250 rpm, with air input at 4.5 liters per liter/minute and at 25 lbs. p.s.i.g. The pH of the fermentation medium changes slightly during the antibiotic production, varying in the range of about 6.8 to about 7.3.

Monitor the antibiotic production using the assay procedure described for sisomicin and when peak production is attained, harvest the product (the fermentation is usually complete in about 7 days).

Peak production for Antibiotics Mu-1, Mu-2, Mu-4, Mu-5, and Mu-6 is in the order of magnitude of from about 5 to about 50 mcg/ml.

EXAMPLE 2

Isolation of Antibiotic Mu-1

Add 7.0g of oxalic acid to the whole broth from Example 1 with stirring. Acidify the broth to pH 2.0 using 6N sulfuric acid. Stir the mixture for about 15 minutes and filter using a suitable filter aid. Neutralize (pH 7.0) the filtrate with 6N ammonium hydroxide. Pass the filtrate through a 1.0 liter cation exchange resin column in the ammonium form (e.g., Amberlite IRC-50, Rohm and Haas, Philadelphia, Pa.). Discard the spent broth and elute the column with 2N ammonium hydroxide collecting fractions of about 100 ml. Monitor the column eluate by disc testing each fraction against Staphylococcus aureus ATCC 6538P. Combine the active fractions and evaporate to about 100 ml. in vacuo and lyophilize to obtain a solid product. Triturate the product several times with warm methanol, filter and evaporate the filtrate to a residue. Chromatograph the product on silica gel (25g) using the lower phase of a chloroform::methanol:concentrated ammonium hydroxide (1:1:1) system as the eluant. Combine and evaporate the fractions containing antibiotic activity to obtain thereby Antibiotic Mu-1.

In a similar manner, by substituting an equivalent quantity of 2,5-dideoxystreptamine, 2-epi-streptamine, 1,3,5-triaminocyclohexene-1,6-diol or 5-epi-2-deoxystreptamine, and by following the procedures of Examples 1 and 2, Antibiotics Mu-2, Mu-4, Mu-5 and Mu-6, respectively, may be produced.

TABLE 6

Disc Test Results (Replicate Tests) with the Antibiotics, Sisomicin and Gentamicin Bauer-Kirby Technique[1] with 10 Mcg. Discs

| Organism | Zone Size (mm) | | | | | |
|---|---|---|---|---|---|---|
|  | Antiobiotic Mu-1 | Antibiotic Mu-2 | Antibiotic Mu-4 | Antiobiotic Mu-5 | Sisomicin | Gentamicin |
| *Escherichia coli* | | | | | | |
| 589 | 29 | 24 | 26 | 18 | 24 | 23 |
| W677/R55 | 30 | 21 | 13 | 10 | 15 | 13 |
| LA290/R55 | 29 | 21 | 16 | ± | 13 | 12 |
| JR88 | 11 | 22 | 16 | 0 | 11 | 11 |
| JR90 | 0 | 25 | 22 | 0 | 0 | 0 |
| Swidinsky 4195 | 28 | 25 | 17 | 0 | 24 | 23 |
| ATCC 10536 | 31 | 28 | 27 | 24 | 28 | 28 |
| Baker 2 | — | — | 24 | — | — | — |
| St. Michael 1574-1 | — | 27 | 25 | 22 | — | — |
| JR66 | — | 26 | 18 | 0 | — | — |
| *Pseudomonas aeruginosa* | | | | | | |
| Stone 20 | 31 | 33 | 28 | 16 | 27 | 27 |
| Stone 39 | 29 | 27 | 20 | 12 | 25 | 25 |
| Stone 130 | 14 | 25 | 14 | 0 | 14 | 12 |
| Stone 138 | 15 | 23 | 11 | 0 | 10 | 10 |
| St. Michael 762 | 24 | 26 | 19 | ± | 25 | 24 |
| St. Michael 1262 | 18 | 27 | 19 | 10 | 26 | 25 |
| St. Michael 1395 | 29 | 28 | 19 | 0 | 26 | 26 |
| St. Michael 413 | 27 | 27 | 19 | 11 | 26 | 26 |
| St. Michael 836 | — | 28 | 19 | 10 | — | — |
| D-2 | 21 | 26 | 17 | 0 | 24 | 23 |
| Capetown 18 | 19 | 22 | 16 | 0 | 14 | 12 |
| *Salmonella typhimurium* | | | | | | |
| Group B | — | 27 | 25 | 22 | — | — |
| *Klebsiella pneumoniae* | | | | | | |
| Ad 17 | 24 | 23 | 25 | 20 | 22 | 22 |
| Ad 18 | 26 | 25 | 24 | 21 | 23 | 25 |
| Ad 22 | — | — | 26 | — | — | — |
| Georgetown 3694 | 26 | 22 | 19 | 0 | 14 | 13 |
| Georgetown 3020 | 26 | 21 | 19 | 0 | 13 | 11 |
| Providence 164 | 15 | 25 | 0 | 9 | 13 | 11 |
| *Staphylococcus aureus* | | | | | | |
| ATCC 6538P | 26 | 27 | 24 | 21 | 25 | 25 |
| Wood | 28 | 29 | 26 | 25 | 29 | 27 |
| Ziegler | 25 | 28 | 24 | 23 | 26 | 26 |
| 59N | 26 | 29 | 26 | 23 | 28 | 28 |

TABLE 6-continued

Disc Test Results (Replicate Tests) with the Antibiotics, Sisomicin and Gentamicin
Bauer-Kirby Technique[1] with 10 Mcg. Discs

| Organism | Zone Size (mm) | | | | | |
|---|---|---|---|---|---|---|
| | Antiobiotic Mu-1 | Antibiotic Mu-2 | Antibiotic Mu-4 | Antiobiotic Mu-5 | Sisomicin | Gentamicin |
| 1118 | — | 14 | 14 | ± | — | — |
| Grey | — | 16 | 13 | ± | — | — |
| Streptococcus pyogenes | | | | | | |
| C | 13 | 15 | 12 | ± | 13 | 13 |
| B-Cruz | 17 | 17 | — | — | 15 | 16 |
| 27 | — | — | 12 | ± | — | — |
| Bacillus subtilis | | | | | | |
| ATCC 6633 | 31 | 33 | 29 | 28 | 31 | 31 |
| Proteus mirabilis | | | | | | |
| Harding | — | 26 | 21 | 19 | — | — |
| Proteus rettgeri | — | 24 | 14 | 13 | — | — |

[1]Bauer, Kirby, Sherris and Turck. American Journal of Clinical Pathology, Vol. 45, pages 493–496 (1966)

Table 7

In Vitro Activity of Antibiotic Mu-1 and Sisomicin
MIC's in Mueller-Hinton Broth pH 7.2
MIC (mcg/ml)

| Organism | Antibiotic Mu-1 | Sisomicin |
|---|---|---|
| Staphlococcus aureus | | |
| ATCC 6538P | 0.3 | 0.08 |
| Wood | 0.08 | 0.03 |
| Ziegler | 0.08 | 0.08 |
| 59N | 0.3 | 0.03 |
| 1118 | 3.0 | 3.0 |
| Grey | 3.0 | 3.0 |
| Streptococcus pyogenes | | |
| C | 3.0 | 3.0 |
| 27 | 7.5 | 3.0 |
| Cruz | 3.0 | 3.0 |
| Alvarez | 7.5 | 3.0 |
| Labay | 7.5 | 3.0 |
| Karipeds | 3.0 | 0.8 |
| Bacillus subtilis | | |
| ATCC 6633 | 0.03 | 0.03 |
| Echerichia coli | | |
| ATCC 10536 | 0.3 | 0.08 |
| Genta. adenyl W677/R55 | 0.8 | 7.5 |
| Kana. phosphor. 589 | 3.0 | 0.8 |
| Kana. phosphor. C-13 | 3.0 | 0.3 |
| Baker 2 | 3.0 | 0.3 |
| F14-Bk | 3.0 | 0.3 |
| Genta. adenyl LA290-R55 | 3.0 | 17.5 |
| Tobra. R 4195 | 3.0 | 0.8 |
| Klebsiella pneumoniae | | |
| Ad 18 | 0.3 | 0.08 |
| Kana. phosphor. Ad 22 | 0.3 | 0.3 |
| Genta. adenyl 3694 | 0.3 | 7.5 |
| Genta. adenyl 3020 | 0.3 | 7.5 |
| Genta. adenyl 121 | 3.0 | 0.08 |
| Pseudomonas aeruginosa | | |
| 1262 | 3.0 | 0.8 |
| 762 | 3.0 | 0.3 |
| 1395 | 3.0 | 0.08 |
| NRRL B3223 | 0.3 | 0.08 |
| D-2 | 0.8 | 0.08 |
| Genta.-Tobra.-R. Travers | >25 | >25 |
| Genta. acetyl Stone 130 | 17.5 | 17.5 |
| Stone 138 | 17.5 | 7.5 |
| Stone 20 | 3.0 | 0.3 |
| Genta. acetyl Capetown 18 | 7.5 | 7.5 |
| Proteus rettgeri | 3.0 | 0.8 |
| Providence | >25 | >25 |
| (Genta R.) 164 | | |
| Salmonella typhimurium | | |
| B | 3.0 | 0.3 |
| Serratia | | |
| 127 | 0.8 | 0.8 |
| Candida albicans | >25 | >25 |
| Trichophyton rubrum | >10 | >25 |
| Aspergillus niger | >10 | >25 |

Table 8

In Vivo Activity of Antibiotic Mu-1 and Sisomicin
Protection Tests in Mice

| Organism | PD$_{50}$ (mg/kg) | |
|---|---|---|
| | Antibiotic Mu-1 | Sisomicin |
| Staphlococcus | | |
| Gray | 6.0 | 1.8 |
| Escherichia coli | | |
| Sc. | 5.0 | 1.7 |
| 6922 | 2.5 | 2.0 |
| Pseudomonas aeruginosa | | |
| 2552 | 15.3 | 2.8 |
| 2557 | 17.1 | 2.7 |
| Sc. | 2.5 | 1.1 |
| Acute Toxicity | | |
| Route | | LD$_{50}$ (mg/kg) |
| I.V. | 110 | 34 |
| I.P. | >700 | 190 |

The antibiotics of this invention are broad spectrum antibacterial agents which may be used for in vitro or in vivo application. For in vitro application, the instant antibiotics may be combined with detergents and used to clean and disinfect the surfaces of laboratory equipment such as tables, scales, cages and the like. For in vivo application, the compounds may be used to treat animals, especially warm blooded animals, having bacterial infections. They are of particular value for treating infections caused by bacteria resistant to aminoglycoside antibiotics used heretofore.

In many instances, bacterial resistance is related to the organism's ability to inactivate the antibacterial agent via enzymatic (biochemical) means. Some species inactivate aminoglycoside antibiotics by acetylating the antibacterial agent, others by phosphorylation and still other by adenylylating. Some strains have several different inactivating capabilities. Further, the inactivation reactions occur at a specific site or sites on the antibacterial agent. We have shown by the compounds of this invention that alteration of sites on the antibiotic molecule not directly involved in inactivation processes can nevertheless frustrate these inactivation processes. The tables evidencing the activity of the disclosed antibiotics include many strains of bacteria exhibiting such resistance. The tables illustrate that the antibiotics of this invention include compounds which are active against strains having different mechanisms of inactivation of gentamicin, sisomicin, kanamycin, neomycin and tobramycin. For example, some antibiotics of this invention are effective against strains of E. coli which contain adenylylating R factors such as E. coli W677/R55 and LA290/R55. These E. coli strains are resistant to gentamicin, sisomicin and tobramycin. Some are also effective against gentamicin, tobramycin and kanamycin resistant adenylylating strains of Klebsiella pneumoniae and also kanamycin, neomycin phosphorylating strains of E. coli and Klebsiella pneumoniae. Further, some antibiotics of this invention are effective against gentamicin and sisomicin resistant strains of Pseudomonas aeruginosa and gentamicin, sisomicin, tobramycin resistant Providence which is sensitive to kanamycin. Thus, Antibiotics Mu-1, Mu-2, Mu-4, Mu-5 and Mu-6 afford a means for combatting strains of bacteria which have already developed a variety of mechanisms for resisting the action of many of the antibiotics known in the art or currently in commercial use.

We claim:

1. A process for producing Antibiotics Mu-1, Mu-2, Mu-4, Mu-5 and Mu-6 which comprises fermenting *Micromonospora inyoensis* strain 1550F-1G in an aqueous nutrient medium, adding to the fermentation a compound of the formula:

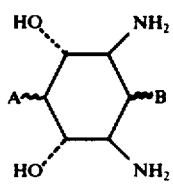

wherein A is a member selected from the group consisting of hydrogen, amino, hydroxy and $(C_1-C_8)$ alkoxy, B is a member selected from the group consisting of hydrogen and hydroxy, wherein the wavy lines connecting A and B to the ring nucleus denote that such groups may be in any of the possible stereoisomeric forms, with the proviso that when B is hydrogen and A is hydroxy, A must be cis to the hydroxyl groups adjacent thereto and with the further proviso that when A is amino, it must be trans to the hydroxy groups adjacent thereto, continuing the fermentation until a composition of matter having substantial antibacterial activity is produced and isolating an antibiotic therefrom.

2. A process according to claim 1 wherein the fermentation is conducted at from about pH 6.0 to about pH 8.0 for about 2 to about 10 days.

3. A process according to claim 2 wherein the fermentation is conducted at from about 24° to about 49° C.

4. A process according to claim 3 wherein the fermentation is conducted at about 35° C for about 7 days from about pH 6.8 to about pH 7.4.

5. The process according to claim 4 wherein the compound added to the fermentation medium is streptamine thereby producing Antibiotic Mu-1.

6. The process according to claim 4 wherein the compound added to the fermentation medium is 2,5-dideoxystreptamine thereby producing Antibiotic Mu-2.

7. The process according to claim 4 wherein the compound added to the fermentation medium is 2-epi streptamine thereby producing Antibiotic Mu-4.

8. The process according to claim 4 wherein the compound added to the fermentation medium is 1,3,5-triaminocyclohexane-4,6-diol thereby producing Antibiotic Mu-5.

9. The process according to claim 4 wherein the compound added to the fermentation medium is 5-epi-2-deoxystreptamine thereby producing 5-epi-sisomicin.

* * * * *